United States Patent
Economides et al.

(10) Patent No.: US 7,205,148 B2
(45) Date of Patent: Apr. 17, 2007

(54) GENOME MUTATION BY INTRON INSERTION INTO AN EMBRYONIC STEM CELL GENOME

(75) Inventors: Aris N. Economides, Tarrytown, NY (US); David M. Valenzuela, Yorktown Heights, NY (US); Samuel Davis, New York, NY (US); George Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 2 days.

(21) Appl. No.: 10/865,424

(22) Filed: Jun. 10, 2004

(65) Prior Publication Data

US 2005/0003543 A1   Jan. 6, 2005

Related U.S. Application Data

(60) Provisional application No. 60/544,453, filed on Feb. 13, 2004, provisional application No. 60/447,652, filed on Jun. 11, 2003.

(51) Int. Cl.
*C12N 15/87* (2006.01)
*C12N 15/05* (2006.01)
*C12N 15/00* (2006.01)

(52) U.S. Cl. ............... 435/462; 435/455; 435/354; 800/25

(58) Field of Classification Search ............... 800/12, 800/25; 435/320.1, 462, 455, 354
See application file for complete search history.

(56) References Cited

U.S. PATENT DOCUMENTS 6,080,576 A * 6/2000 Zambrowicz et al.
6,270,989 B1 * 8/2001 Treco et al. ............... 435/69.1
6,524,818 B1 * 2/2003 Harrington et al. ......... 435/69.1

OTHER PUBLICATIONS

Xu et al, Conditional mutation of Brca1 inmammary epithelial cells results inblunte ductal morphogensis an tumor formation, Nature Genetics, 22: 37-43, 1999.*
Buehr et al, Genesis of embryonic stem cells, Phil Trans R Soc Lond, 358: 1397-1402, 2003.*
Filip et al, Adult stem cells and their importance in cell therapy, Folia Biol (Praha), 49(1): 9-14, 2003, abstract.*
Gorba et al, Pharmacological potential of embryonic stem cells, Pharmacolgical Research, 47: 269-278, 2003.*
Work et al, Targeting gene therapy vectors to the vascular endothelium, Curr Atheroscl, 5(3): 163-70, 2003, abstract.*
Romano, Gene transfer in experimental medicine, Drug News Perspec, 16(5): 265, abstract.*
Romano, Systems for regulated or tissue-specific gene expression, Drug News Perspec, 17(2): 85-90, 2004.*
Buehr et al, Phil Tran R Soc Lond, 358: 1397-1402, 2003.*
Pharmacol Res, 47(4): 269-78, Apr. 2003.*
Reubinoff et al, Nature Biotechnology, 18:399-404, 2000.*
Romano, Drug News Perspect, 16(5): 267, 2003.*
Denning et al, Reproduction, 126: 1-11, 2003.*
Forlino et al, JBC, 274(53): 37923-37931, 1999.*
Liu et al, Genome Research, 13(3): 476-84 Mar. 2003.*
Zhang et al, (Nucleic Acids Research, 30(17): e90, 2002.*
Capechi et al, Scientific American, 52-59, 1994.*
Zhang, Z., et al., 2002, "Cre Recombinase-Mediated Inversion Using Lox66 and Lox71: Method to Introduce Conditional Point Mutations Into the CREB-Binding Protein", Nucleic Acids Research 30(17) e90.
Pelanda; R., et al., 2002, "Cre Recombinase-Controlled Expression of the mb-1 Allele". Genesis 32:154-157.
Wu, et al., 1997, "Methods in Gene Biotechnology, chapter 17: New Strategies for gene Knockout" Methods in gene Biotechnology, vol. 17, 1997, pp. 339-365, XP002959374.
Lewin, B., et al., (1997) Genes VI, Oxford Univ. Press Chapter 22, pp. 663-667, and p. 1227.
Burge, C., et al., (1999) The RNA World, Cold Spring Harbor Press, Chapter 20, pp. 525-560.

* cited by examiner

*Primary Examiner*—Deborah Crouch
*Assistant Examiner*—Magdalene K. Sgagias
(74) *Attorney, Agent, or Firm*—Valeta Gregg, Esq.; Ying-Zi Yang (57) ABSTRACT

Methods of creating mutations in genomic exons by inserting introns into the genomic exons via homologous recombination. Also, methods are provided for introducing modifications into genomic exons by inserting introns into the genomic exons via homologous recombination such that a mature mRNA transcript produced from a genomic region of the genome comprising the genomic exon does not contain the modification are provided. The methods provide for a rapid method for introducing mutations and/or modifications of any type into a mammalian cell genome.

9 Claims, 6 Drawing Sheets

GENOME MUTATION BY INTRON INSERTION INTO AN EMBRYONIC STEM CELL GENOME

CROSS-REFERENCE TO RELATED APPLICATIONS

This application claims the benefit under 35 USC § 119(e) of U.S. Provisional 60/477,652 filed 11 Jun. 2003 and 60/544,453 filed 13 Feb. 2004, which applications are herein specifically incorporated by reference in their entirety.

FIELD OF THE INVENTION

The field of the invention is related to methods of mutating or modifying genomic exons in eukaryotic cells. In particular, the field of the invention is methods of mutating or modifying genomic exons in eukaryotic cells comprising introducing engineered (artificial) introns into the genomic exons.

DESCRIPTION OF RELATED ART

Zhang et al. (2002) Nucleic Acids Research 30(17) e90) describe a method to introduce conditional point mutations into the CREB-binding protein with Cre recombinase-mediated inversion using Lox66 and Lox71. Pelanda et al. (2002) Genesis 32:154–157 describe Cre-recombinase-controlled expression of mb-1 allele.

BRIEF SUMMARY OF THE INVENTION

The methods of the invention are based on the finding that the introduction of an intron into a genomic exon in a eukaryotic cell genome provides a rapid method for introducing mutations and/or modifications of any type into the cell genome.

Accordingly, a first aspect of the invention is a method creating a mutation in a genomic exon in the genome of a eukaryotic cell, comprising introducing an intron into the genomic exon by homologous recombination such that a mutation is created in the genomic exon.

Although specific embodiments of the method of the invention encompass the introduction of a naturally existing intron, generally the introduced intron will be artificial, e.g., engineered to contain specifically-desired sequences. In one embodiment, the introduced intron comprises at least one site-specific recombination site. In another embodiment, the intron comprises at least two site-specific recombination sites. In a specific embodiment, the site-specific recombination sites are oriented in the same direction with respect to one another such that excision of the DNA sequence between them occurs as a result of site-specific recombination. In another specific embodiment, the site-specific recombination sites are oriented in the opposite direction with respect to one another such that inversion of the DNA sequence between them occurs as a result of site-specific recombination. In yet another specific embodiment, four site-specific recombination sites are utilized in pairs, in such a manner that each pair is oriented in the opposite direction with respect to one another and in the following order: A—spacer sequence—B/intervening sequence/(A)—spacer sequence—(B), where A and B are heterospecific recombination sites, and parenthesis indicates reverse complement orientation. The result of site-specific recombination between these sites will be inversion of the DNA sequence between them to give rise to a rearranged sequence of the structure A/intervening sequence/(B). Depending on the choice of sites utilized, no further site-specific recombinase-mediated recombination can take place between A and (B), but the resulting sequence may be amenable to Recombinase-Mediated Cassette Exchange (RMCE). In yet another embodiment, the intron contains a selection cassette that may be flanked by site-specific recombinase sites. This cassette may be located in the sense or the antisense strand of the sequence contained within the intron.

In a preferred embodiment, the eukaryotic cell is a mammalian cell. In another embodiment, the mammalian cell is a rat, mouse, rabbit, cat, dog, cow, sheep, goat, pig, or horse cell. In still another embodiment, the rat, mouse, rabbit, cat, dog, cow, sheep, goat, pig, or horse cell is an embryonic stem cell. In a specific embodiment, the embryonic stem cell is mouse embryonic stem cell.

In another embodiment, the method of the invention further optionally comprises introducing the embryonic stem cell comprising the mutated genomic exon into a blastocyst; and introducing the blastocyst into a surrogate mother for gestation of offspring having the mutated genomic exon. Still another embodiment of the invention further optionally comprises exposing the offspring to a recombinase that recognizes the site-specific recombination sites such that the sequence between the site-specific recombination sites is excised or inverted. In a specific embodiment, the embryonic stem cells are mouse embryonic stem cells and the offspring are mice.

Other particular embodiments of the invention are ones wherein the mutation is an insertion, deletion, or substitution of one or more nucleotides; the modification is an insertion of one or more exogenous DNA sequences; or the mutation is an insertion, deletion, or substitution of one or more nucleotides and the modification is an insertion of one or more exogenous DNA sequences.

A specific embodiment is one wherein the site-specific recombination sites are loxP sites. An alternative specific embodiment is one wherein the site-specific recombination sites are FRT sites. In a particular specific embodiment, the recombinase is Cre and the site-specific recombination sites are LoxP sites; and in still another particular specific embodiment, the recombinase is Flp and the site-specific recombination sites are FRT sites.

A second aspect of the invention provides a method of introducing a modification into a genomic exon in the genome of a mammalian cell, comprising introducing an intron into a genomic exon by homologous recombination such that a mature mRNA transcript produced from a genomic region of the genome comprising the genomic exon does not contain the modification.

In one embodiment of this second aspect of the invention, the intron comprises at least one site-specific recombination site. In still another embodiment of this aspect of the invention, the method further optionally comprises inserting a site-specific recombination site into a region outside of the genomic exon by homologous recombination. In a particular embodiment, the site-specific recombination site in the intron and the site-specific recombination site in the region outside of the genomic exon are oriented in the same direction with respect to one another such that excision of the DNA sequence between them occurs as a result of site-specific recombination.

Another specific embodiment is one wherein the method further optionally comprises introducing an embryonic stem cell comprising the genomic exon containing the modification into a blastocyst; and introducing the blastocyst into a surrogate mother for gestation of offspring having the modified genomic exon, and further optionally comprising exposing the offspring to a recombinase that recognizes the site-specific recombination sites such that the sequence between the site-specific recombination sites is inverted.

A third aspect of the invention is a method of introducing a transcriptional termination signal sequence into a genomic exon in the genome of a mammalian cell, comprising introducing an intron comprising a transcriptional termination signal sequence into the genomic exon by homologous recombination such that the transcriptional termination signal sequence—usually a polyadenylation signal sequence—is placed in the antisense strand of the intron, and therefore mature mRNA transcripts produced from the genomic exon thus modified, do not contain the transcriptional termination signal sequence.

One embodiment of this aspect is wherein the intron comprises at least two site-specific recombination sites; another embodiment is wherein the site-specific recombination sites flank the transcriptional termination signal sequence; and still another embodiment is wherein the site-specific recombination sites are oriented in the opposite direction with respect to one another such that inversion of the transcriptional termination signal sequence occurs as a result of site-specific recombination.

A fourth aspect of the invention is a method of introducing a transcriptional termination signal sequence into a genomic exon in the genome of a mammalian cell, comprising introducing an intron comprising a transcriptional termination signal sequence into the genomic exon by homologous recombination such that the transcriptional termination signal sequence—usually a polyadenylation signal sequence—is placed in the antisense strand of the intron. The transcriptional termination signal sequence is flanked by four site-specific recombination sites utilized in pairs, in a manner such that each pair is oriented in the opposite direction with respect to one another and in the following order: A—spacer sequence—B/transcriptional termination signal sequence/(A)—spacer sequence—(B), where A and B are heterospecific recombination sites, and parenthesis indicates reverse complement orientation. The result of site-specific recombination between these sites is inversion of the transcriptional termination signal sequence between them to give rise to a rearranged sequence of the structure A/transcriptional termination signal sequence/(B), where the transcriptional termination signal sequence is located in the sense strand of the intron.

Other objects and advantages will become apparent from a review of the ensuing detailed description.

BRIEF DESCRIPTION OF THE FIGURES

FIG. 1: Exemplary schematic diagram for mutating an exon by introducing an intron. GOI=gene of interest; GOI*=mutated gene of interest; pA=polyadenylation sequence; SD=splice donor; SA=splice acceptor; LoxP=site-specific recombination site recognized by Cre recombinase; PGKp/EM7p=phosphoglycerate kinase promoter/EM7 promoter shown in reverse to indicate antisense orientation; Hyg-TK=hygromycin-thymidine kinase selectable marker genes shown in reverse to indicate antisense orientation; Cre=Cre recombinase that recognizes LoxP sites; GANG$^S$=ganciclovir-sensitive; GANG$^R$=ganciclovir-resistant; Hyg$^R$=hygromycin-resistant; Hyg$^S$=hygromycin-sensitive; rectangle shaded left dark to right light=5' homology box (for BHR); rectangle shaded left light to right dark=3' homology box (for BHR). Downward arrow at step 1: cloning of BHR or other suitable method to generate targeting vector (e.g., select for Hyg-resistance); downward arrow at step 2: introducing targeting vector into ES cells and selected targeted clones (select for Hyg-resistance; screen for targeted clones); downward arrow at optional step 3: Cre and select in gangciclovir.

FIG. 2A: Abbreviations are the same as FIG. 1. The features of the modified intron as the same as described in example 1, except that the selection cassette is not only floxed but also flanked by FRT sites ("flrted"), which are recognized by the Flip recombinase (Flp). This feature allows for an additional choice for removing the selection cassette. An alternative strategy is to use Cre and select for cells where only the desired event has taken place, i.e., only the selection cassette has been deleted. Downward arrow at steps 1 and 2 same as FIG. 1: downward arrow at optional step 3 (FIG. 2A) or optional step 1 (FIG. 2B): Flp and select in gangciclovir; downward arrow at step 2 (FIG. 2B): introduce into animals to generate animals with genotype that is GOI*/+; downward arrow at step 3 (FIG. 2B): breed to appropriate Cre detector. Exon 2a (bearing dominant mutation) has been deleted. Genotype is GOI −/+: no phenotype (except in haploinsufficiency).

FIG. 3A–C: Exemplary schematic diagram for generating a conditional allele by introducing an intron containing a conditional transcriptional termination signal. LoxL=Lox66 site-specific recombination mutant site recognized by Cre recombinase; LoxR=Lox71 site-specific recombination mutant site recognized by Cre recombinase; LoxL/R=Lox66/71 site-specific recombination double mutant site (is not recognized by Cre recombinase); FRT=site-specific recombination site recognized by Flp recombinase; Cre=Cre recombinase that recognizes LoxP, Lox66, and Lox71 sites; eGFP=enhanced Green Fluorescent Protein. FIGS. 3A-C: downward arrow at step 2: Flp; select for ganciclovir resistant cells; downward arrow at step 3: Cre (in cells or animals) Original gene message terminates prematurely and only exon 1a+eGFP are part of the new mRNA.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the"include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe the methods and/or materials in connection with which the publications are cited.

Definitions

By "conditional allele" as used herein is meant an allele of a gene that has been modified from its native sequence such that the sequence of the mRNA encoded by the modified gene can be controlled and/or altered upon supply of a specific signal, or is conditional upon, another event.

By "artificial," "engineered," or "modified" intron as used herein is meant a predefined intron sequence that has been altered from its native sequence either by deletions of some of its sequences or by addition of DNA sequences including but not limited to promoters, regulatory elements, polyadenylation signal sequences, coding sequences, site-specific recombination sites, selectable marker genes, reporter genes, and other genes of interest engineered. Any of the aforementioned elements may be placed either in the sense or the antisense strand of the intron sequence.

By "targeting vector" as used herein is meant a DNA construct that contains sequences "homologous" to endogenous chromosomal nucleic acid sequences flanking a desired genetic modification(s). The flanking homology sequences, referred to as "homology arms", direct the targeting vector to a specific chromosomal location within the genome by virtue of the homology that exists between the homology arms and the corresponding endogenous sequence and introduce the desired genetic modification by a process referred to as "homologous recombination". By "homologous" as used herein is meant two or more nucleic acid sequences that are either identical or similar enough that they are able to hybridize to each other or undergo intermolecular exchange.

By "gene targeting" as used herein is meant the modification of an endogenous chromosomal locus by the insertion into, deletion of, or replacement of the endogenous sequence via homologous recombination using a targeting vector.

By "modification cassette" as used herein is meant a stretch of DNA, typically linear, which contains any combination of DNA sequences including promoters, regulatory elements, coding sequences, polyadenylation sequences, splice acceptor/splice donor sequences, etc., that will modify a target DNA once it is inserted into it. Such insertion can occur by any means including but not limited to homologous recombination.

By "recombinase" as used herein is meant an enzyme that recognizes specific nucleotide sequences termed "recombination sites" or "site-specific recombination sites" which catalyzes recombination of DNA between these sites. Recombinases are able to either delete sequences between the site-specific recombination sites if the sites are oriented in the same direction with respect to one another or invert the sequences between the site-specific recombination sites if the sites are oriented in opposite directions with respect to one another.

By "heterospecific recombination site" as used herein is meant a site-specific recombination site that is mutated in the asymmetric spacer region of its sequence. As a general rule two heterospecific recombination sites with different spacer sequences do not recombine with one another in the presence of their cognate recombinase.

General Description

The methods of the invention are directed to (1) methods of creating mutations in genomic exons by inserting introns into the genomic exons, and/or (2) introducing modifications into genomic exons by inserting introns into the genomic exons such that a mature mRNA transcript produced from a genomic region of the genome comprising the genomic exon does not contain the modification, and/or (3) where all or some of the introduced modifications can be incorporated into the mature mRNA transcript after another signal has been provided. In a specific embodiment, the methods of the invention are achieved via homologous recombination. The methods of the invention provide for a rapid method for introducing mutations and/or modifications of any type into a eukaryotic cell genome. Further, the methods of the invention may be practiced with any cell or organism that has RNA splicing mechanisms.

Selection of Gene(s) and/or Locus(loci)

A variety of approaches can be used for selecting a gene or locus of interest for genetic mutation and/or modification of its genomic exon(s). For example, the selection approach can be based on specific criteria such as detailed structural or functional data, or it can be selected in the absence of such detailed information as potential genes or gene fragments become predicted through the various genome sequencing projects. It should be noted that it is not necessary to know the complete sequence and gene structure of a gene or locus of interest to apply the methods of the invention.

Genetic Mutations/Modifications

One type of modification envisioned in the current invention is the introduction of mutations in exonic sequences or in sequences near an exon. The genetic mutations and/or modifications that may be made to exon(s) in the selected genes include but are not limited to silent mutations (i.e. they do not translate into amino acid changes in the sequence normally encoded by the genomic exon), point mutations (i.e. nucleotide substitutions) that result in a single amino acid change within the coding sequence of the exon, or more extensive changes such as insertions or deletions of one or more nucleotides, multiple amino acid changes, or insertion of (exogenous) DNA sequences. Non-limiting examples of changes/mutations that can be made include any one or any combination of the following:

(a) insertion of sequences into an exon, where the introduced sequence may include non-coding sequences, or coding sequences (including but not limited to epitope tags, i.e., myc tags, His tags, HA tags, or any other sequences inserted in frame to result in fusion proteins);

(b) deletions of one or more bases of sequence residing in an exon;

(c) deletions of coding sequence residing in an exon;

(d) changes in the coding or non-coding sequence of an exon, including point mutations (which may or may not be silent) or changes of multiple but not necessarily consecutive bases;

(e) changes in the non-exonic sequence on either side of an exon, including point mutations or changes of multiple but not necessarily consecutive bases;

(f) deletions or insertions in non-exonic sequence on either side of an exon;

(g) combinations and permutations of (a)–(f) above.

Another type of modification envisioned in the current invention is the use of introns in engineering, designing, and/or generating recombinase-controlled or -dependent conditional alleles. Examples of this embodiment include the introduction of an artificial intron into an exon, where the intron may contain any combination of the following elements:

(a) site-specific recombination sites (for example, LoxP sites recognized by Cre, FRT sites recognized by Flp, or other recombination site/recombinase system known to the art) flanking a sequence of interest such that the flanked sequence:

(i) Can be excised after exposure to the appropriate recombinase if the site-specific recombinase sites are placed in the same orientation as defined by their asymmetric core region, or (ii) Can be inverted after exposure to the appropriate recombinase if the site-specific recombinase sites are placed in the opposite orientation with respect to one another as defined by their asymmetric core region.

(b). Selectable marker genes or selection markers that allow for the isolation of rare transfected cells expressing the marker from the majority of treated cells in the population including, but are not limited to, neomycin phosphotransferase (neo), hygromycin phosphotransferase (hygro), puromycin-N-acetyl-transferase (puro), or other marker genes that provide other types of selection cues, such as LacZ or fluorescing proteins such as GFP;

(c) polyadenylation (polyA) sequences that can function as transcription termination signals.

The conditionality is brought about through the design of the new allele and the combination of elements chosen to be placed within the intron and/or downstream or upstream the modified exon. Depending on the design, either one of two things may happen after exposure to a recombinase:

(a) deletion of the part of the intron and part of the exon that are flanked by recombinase recognition sequences, or (b) inversion of the part of the intron and/or part of the exon that are flanked by recombinase recognition sequences.

Nucleic Acid Constructs

The techniques used to obtain the components of the artificial introns and to construct the targeting vectors containing the introns and other elements described herein are standard molecular biology techniques well known to the skilled artisan (see e.g., Sambrook et al. (1989) Molecular Cloning: A Laboratory Manual, Second Edition, Vol. 1–3). All DNA sequencing is done by standard techniques using an ABI 373A DNA sequencer and Taq Dideoxy Terminator Cycle Sequencing Kit (Applied Biosystems, Inc., Foster City, Calif.).

The introduced introns and the components contained therein that are useful in practicing the methods of the invention can be constructed in a variety of ways. Any intron sequence may be suitable for use in the methods of the invention, although introns that have been sequenced and characterized are most useful. An example of a suitable, sequenced and characterized intron includes but is not limited to the rabbit beta-globin intron 2. Once an intron is chosen, it can be subsequently engineered to contain any number of different exogenous DNA sequences. Examples of exogenous DNA sequences that may be inserted into the intron include, but are not limited to, site-specific recombination sites (i.e. LoxP sites, FRT sites, other naturally occurring site-specific recombination sites, as well as mutated versions of the site-specific recombination sites that can undergo recombination when exposed to the appropriate recombinase, but which after recombination result in a genetic change that is not reversible by further treatment with the same recombinase). The site-specific recombination sites can be inserted into the intron in such a way as to be oriented in the same direction with respect to one another, which will result in excision of any intervening DNA sequence following exposure to the appropriate recombinase, or they can be oriented in opposite directions with respect to one another, which will result in inversion of any intervening DNA sequence following exposure to the appropriate recombinase. In addition the intron can be constructed such that one site-specific recombinase in within it, and a second one is located outside the intron. Any desirable orientation of the sites with respect to one another is also contemplated; selectable marker genes or Open Reading Frames (ORFs) such as those encoding for neo, hygro, or puro, as well as negative selection genes such as Herpes Simplex Virus thymidine kinase (HSV-tk) and fusions of HSV-tk with neo, hygro or puro, or other selectable marker genes familiar to skilled artisans may also be engineered into the intron. These selectable markers may or may not be under the transcriptional control of an exogenous promoter, such as PGK or human ubiquitin C promoter. It is also possible to include reporter genes or reporter ORFs within the introns, including LacZ or those encoding for fluorescing proteins such as GFP or others familiar to skilled artisans. Such selection marker genes and reporter genes may or may not be flanked by sites recognized by recombinases; polyadenylation (polyA) sequences (which also function as transcriptional termination signal sequences) may also be included within the introns as well as other sequences capable of turning on, turning off, enhancing, down-regulating or otherwise modulating gene expression. The exogenous sequences contained within the intron may be oriented in either the sense or antisense direction with respect to the genomic exonic sequence into which it will be inserted. If more than one exogenous sequence is contained in the intron, the sequences can be in the same or opposite direction with respect to one another and they may be either sense, antisense or a combination of both with respect to the genomic exonic sequence.

In one non-limiting example, a polyA sequence is placed in the antisense strand with respect to the transcriptional unit/gene/locus in which it is being inserted, and it is flanked by two LoxP sites that are oriented in opposite directions with respect to one another. Following exposure to a Cre recombinase, the polyA sequence will be inverted and will be capable of terminating transcription of any expressed/transcribed sequence that may be upstream of it, resulting is a truncated transcript. In the absence of Cre, the polyA sequence will have no effect on the expressed/transcribed sequence upstream of it and a normal transcript will be generated. The examples set forth below illustrate several non-limiting examples of how such sequences can be utilized in practicing the methods of the invention.

In another non-limiting example, a 3' splice site element together with a polyA sequence (SA-polyA) are placed in the antisense strand with respect to the transcriptional unit/gene/locus in which they are being inserted. As in the previous embodiment, they are flanked by two LoxP sites that are oriented in opposite directions with respect to one another. Following exposure to a Cre recombinase, the polyA sequence will be inverted and will be capable of terminating transcription of any expressed/transcribed sequence that may be upstream of it, resulting is a truncated transcript. In the absence of Cre, the SA-polyA sequence will have no effect on the expressed/transcribed sequence upstream of it and a normal transcript will be generated. The examples set forth below illustrate several non-limiting examples of how such sequences can be utilized in practicing the methods of the invention.

In yet another related non-limiting example, a 3' splice site element together with a marker ORF followed by a polyA sequence (SA-marker-polyA) are placed in the antisense strand with respect to the transcriptional unit/gene/ locus in which they are being inserted. As in the afforementioned embodiment, they are flanked by two LoxP sites that are oriented in opposite directions with respect to one another. Following exposure to a Cre recombinase, the polyA sequence will be inverted and will be capable of terminating transcription of any expressed/transcribed sequence that may be upstream of it, resulting is a truncated transcript that encodes for a hybrid gene product composed of the marker coding sequence C-terminally fused to the sequence preceding it that originates from the target gene. In the absence of Cre, the SA-marker-polyA sequence will have no effect on the expressed/transcribed sequence upstream of it and a normal transcript will be generated. The examples set forth below illustrate several non-limiting examples of how such sequences can be utilized in practicing the methods of the invention.

In another embodiment, the Lox sites utilized are right element (RE) and left element (LE) mutant Lox sites such as Lox66 and Lox71, and as such have the property that after Cre-mediated inversion they will give rise to a double mutant Lox site LoxRE/LE and a LoxP site. This combination is resistant to further rearrangement by Cre, thereby rendering the inversion of the LoxRE/LoxLE-flanked sequence irreversible. Another means of achieving an irreversible inversion is the use of heterospecific LoxP sites (sites that have identical inverted repeat arms but differ in the core spacer region). In this case a combination of 2 heterospecific sites is envisioned where they flank the sequence to be inverted. A cassette of the following configuration is utilized: A—spacer sequence—B/sequence to be inverted/(A)—spacer sequence—(B), where A and B are the heterospecific recombination sites, and parenthesis indicates reverse complement orientation. The result of site-specific recombination between these sites will be inversion of the sequence between them to give rise to a rearranged sequence of the structure A/transcriptional termination signal sequence/(B), where the transcriptional termination signal sequence is located in the sense strand of the intron. Both RE, LE, and heterospecific sites have been developed for other recombinases and are equally applicable to this invention.

One standard molecular biology technique useful in practicing in the methods of the invention is bacterial homologous recombination. Bacterial homologous recombination, also commonly referred to as "recombineering", can be performed in a variety of systems (see for example Yang et al. (1997) Nat Biotechnol, 15:859–65). One example of a system currently in use is ET cloning (see for example Zhang et al. (1998) Nat Genet, 20:123–8) and variations of this technology (see for example Yu et al. (2000) Proc Natl Acad Sci USA, 97:5978–83.

Introduction of DNA into Eukaryotic Cells

The DNA, including DNA targeting vectors and other types of DNA such as linear segments of DNA or cicular plasmids, useful in practicing the methods of the invention can be introduced into eukaryotic cells using standard methodologies such as transfection mediated by calcium phosphate, lipids, or electroporation (Sambrook et al. (1989) supra). The cells in which the DNA has been introduced successfully can be selected by exposure to any number of selection agents, depending on the selectable marker gene that has been engineered into the introduced DNA. As a non-limiting example, if the selectable marker gene is the neo gene, then cells that have taken up the DNA can be selected in G418-containing media; cells that have not taken up the DNA that carries neo will die whereas cells that have taken up that DNA will survive. Other suitable selectable markers include any agent that has activity in appropriate eukaryotic cells such as hygromycin B, or puromycin, as well as other agents familiar to those skilled in the art.

Identification of Genetically Mutated and/or Modified Eukaryotic Cells

As described in U.S. Pat. No. 6,586,251 (Eonomides et al.), which publication is herein specifically incorporated by reference, mammalian cells modified by the methods of the invention can be identified using a variety of approaches and assays. Such approaches and assays can include but are not limited to: (a) quantitative PCR using TaqMan® (Lie et al. (1998) Curr Opin Biotechnol, 9:43–8); (b) quantitative assay using molecular beacons (Tan et al. (2000) Chemistry 6:1107–11); (c) fluorescence in situ hybridization FISH (Laan et al. (1995) Hum Genet 96:275–80) or comparative genomic hybridization (CGH) (Forozan et al. (1997) Trends Genet, 13:405–9); (d) isothermic DNA amplification (Lizardi et al. (1998) Nat Genet, 19:225–32); and (e) quantitative hybridization to an immobilized probe(s ) (Southern (1975) J. Mol. Biol. 98:503).

In one illustrative example, TaqMan® quantitative PCR is used to screen for successfully targeted mammalian cells which have undergone homologous recombination wherein a portion of one of two endogenous alleles in a diploid genome has been altered in some way or replaced by another sequence. TaqMan® method will detect the modification of one allele by measuring the reduction in copy number (by half) of the unmodified allele. Specifically, the probe detects the unmodified allele and not the modified allele. Therefore, the method is independent of the exact nature of the modification and not limited to the sequence replacement described in this example. TaqMan is used to quantify the number of copies of a DNA template in a genomic DNA sample, especially by comparison to a reference gene (Lie et al. (1998) supra). The reference gene is quantitated in the same genomic DNA as the target gene(s) or locus(loci). Therefore, two TaqMan® amplifications (each with its respective probe) are performed. One TaqMan® probe determines the "Ct" (Threshold Cycle) of the reference gene, while the other probe determines the Ct of the region of the targeted gene(s) or locus(loci) which is replaced by successful targeting. The Ct is a quantity that reflects the amount of starting DNA for each of the TaqMan® probes, i.e. a less abundant sequence requires more cycles of PCR to reach the threshold cycle. Decreasing by half the number of copies of the template sequence for a TaqMan® reaction will result in an increase of about one Ct unit. TaqMan® reactions in cells where one allele of the target gene(s) or locus(loci) has been replaced by homologous recombination will result in an increase of one Ct for the target TaqMan® reaction without an increase in the Ct for the reference gene when compared to DNA from non-targeted cells. This allows for ready detection of the modification of one allele of the gene(s) of interest in mammalian cells.

A second alternative example of an assay suitable for identifying correctly targeted cells termed a loss of polymorphic allele assay is further illustrated. Diploid organisms contain two copies of every chromosome, and therefore two copies of every gene. However, all populations contain a certain amount of genetic diversity, and as a result, small differences often exist between the two copies of any particular gene. A common type of genetic diversity is represented by single nucleotide polymorphisms (SNPs). SNPs usually have no phenotypic consequence, so there is no selective pressure to remove them from a population. Thus, they can be found at a reasonable density throughout the genome (about one every 1,000 base pairs) in natural populations. Several robust methods have been developed to detect SNPs for the purpose of mapping linked alleles attributable to phenotype of interest. Inbred mouse strains have been established by many generations of brother-sister matings in order to greatly reduce the normal genetic diversity. The two copies of any given gene have a much higher likelihood of being identical within these strains, however the frequency of genetic variation, like SNPs, between different inbred strains is the same (about one every 1,000 base pairs) as in the general mouse population. With the advent of whole-genome sequencing, it is now possible to detect SNP, or any other genetic, differences between inbred strains. In fact, high-density maps of the majority of SNPs between several major mouse strains are now available. Applicants and others have established embryonic stem cell lines (ES cell lines) from embryos derived from an intercross between two different inbred strains, so called F1 ES cells. Every autosomal gene in these F1 ES cell lines is present in one copy from one parental strain and one copy from the other strain. Upon determination of the SNPs between the two strains for a gene of interest, any of the methods developed to detect SNPs would allow one to detect the loss of either of the two strain-specific alleles of that gene following gene targeting.

Use of Genetically Mutated and/or Modified Eukaryotic Cells

The mutated and/or modified eukaryotic cells generated by the methods of the invention can be employed in any in vitro or in vivo assay. For example, the cells may be used for protein production, gene therapy, or in cell based assays such as drug discovery screening assays.

The genetically modified eukaryotic cells generated by the methods of the invention can also be used to generate an organism carrying the genetic modification. The genetically modified mammalian cells can be used to generate organisms by several different techniques including but not limited to (a) modified embryonic stem (ES) cells such as the frequently used rat and mouse ES cells. These rat and mouse ES cells can be used to create genetically modified rats or mice by standard blastocyst injection technology or aggregation techniques (see for example Robertson, Practical Approach Series, 254, 1987), tetraploid blastocyst injection (see Wang et al. (1997) Mech Dev 62:137–45), or nuclear transfer and cloning (Wakayama et al. (1999) Proc. Natl. Acad. Sci. USA 96:14984–9). ES cells derived from other organisms such as rabbit, cat, dog, cow, sheep, goat, pig, or horse or other non-human mammals are also amenable to genetic modification(s) using the methods of the invention; (b) modified protoplasts can be used to generate genetically modified plants (see, for example, U.S. Pat. Nos. 5,350,689 and 5,508,189); (c) nuclear transfer from modified mammalian cells to oocytes to generate cloned organisms with modified alleles (see for example Wakayama et al. (1999) supra); (d) cell-fusion to transfer the modified allele to another cell, including transfer of engineered chromosome (s), and uses of such cell(s) to generate organisms carrying the modified allele or engineered chromosome(s) (see Kuroiwa et al. (2000) Nat. Biotechnol. 18:1086–1090).

Genetically Mutated and/or Modified Non-human Organisms

In one embodiment, the invention is drawn to a transgenic animal which possesses a recombinant nucleic acid encoding a marker gene within its genome. Such a recombinant nucleic acid can comprise, for example, a nucleic acid encoding a marker gene (e.g., lacZ) that is operably linked to a promoter and/or enhancer from an endogenous gene. Detection of the marker gene can, for example, comprise staining a tissue sample obtained from a transgenic animal which expresses the marker gene, with a substance appropriate for detection of expression of the marker gene. Suitable marker genes and techniques for detection are described herein and/or are well known in the art.

One use of a transgenic animal having a marker gene is a method for testing an effect of an agent (e.g., a drug, a nucleic acid, a gene product, a targeting molecule) on a particular biological response. The method can comprise administering the agent to a transgenic animal (e.g., a mouse, including an embryo, a neonate, a juvenile, an adult) having a marker gene inserted in a gene of interest, and observing the effect of the agent on the biological activity associated with the gene of interest, as compared to the effect in a suitable control transgenic animal having the marker gene and maintained under identical conditions, but not administered the agent.

In one embodiment, the invention is drawn to a knockout animal in which the expression of a gene of interest within its genome has been interrupted. One use of a knockout animal in which the expression of a gene of interest within its genome has been interrupted is as an animal model system for diseases and conditions associated with the function of the knocked out gene of interest. Such a model system is also used for identifying therapeutic agents and/or treatments of the diseases and conditions. The present invention also relates to a method for identifying therapeutic agents for treatment of an individual diagnosed with a clinical disorder associated with a mutation in the gene of interest in which normal expression is altered or otherwise abnormal. The knockout animal is administered a candidate therapeutic agent and is then assayed for therapeutic effects resulting from the administration of the candidate therapeutic agent, as determined from the use of appropriate experimental controls. Therapeutic effects are indicated by a reduction or reversal of symptoms or amelioration of the general condition of the knockout animal. Screening of candidate therapeutic agents such as small molecules from molecular libraries, presently known drugs, and molecules for use in gene therapy, will identify therapeutic agents for treatment of a human patient diagnosed with a disorder similar to that of the animal model used. This model system can also be used for the identification of optimal methods of delivery and vectors for use in the gene therapy methods described above. This method can also be adapted to identify agents which prevent the development of a clinical disorder in an individual with a disorder associated with the gene of interest, for instance by administering the candidate agent to an asymptomatic knockout animal, and then subjecting the animal to conditions expected to bring on the disorder.

In another embodiment, the invention is drawn to the generation of animals that possess conditional alleles. Conditional alleles as used herein means an allele of a gene that has been modified from its native sequence such that its expression, or lack thereof, is controlled by, or is conditional upon, another event. As a non-limiting example, flanking a gene or a portion of a gene with site-specific recombination sites such as loxP sites and then exposing the animal containing the flanked gene or portion of a gene to a recombinase that recognizes the site-specific recombination sites results in either excision or inversion of the flanked sequence, depending on the orientation of the site-specific recombination sites. This excision or inversion is conditional upon exposure to the recombinase. Other uses for genetically modified non-human organisms, especially transgenic and knockout organisms, for example transgenic and knockout mice, are familiar to skilled artisans.

Other features of the invention will become apparent in the course of the following descriptions of exemplary embodiments which are given for illustration of the invention and are not intended to be limiting thereof.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Mutating an Exon by Introducing an Intron

While a gene having any number of exons is amenable to the methods of the invention, for illustrative purposes only, the example described herein utilizes a hypothetical gene having three exons. It is understood by skilled artisans that the number of exons is not relevant to the practice of the methods described herein.

Figure 1:
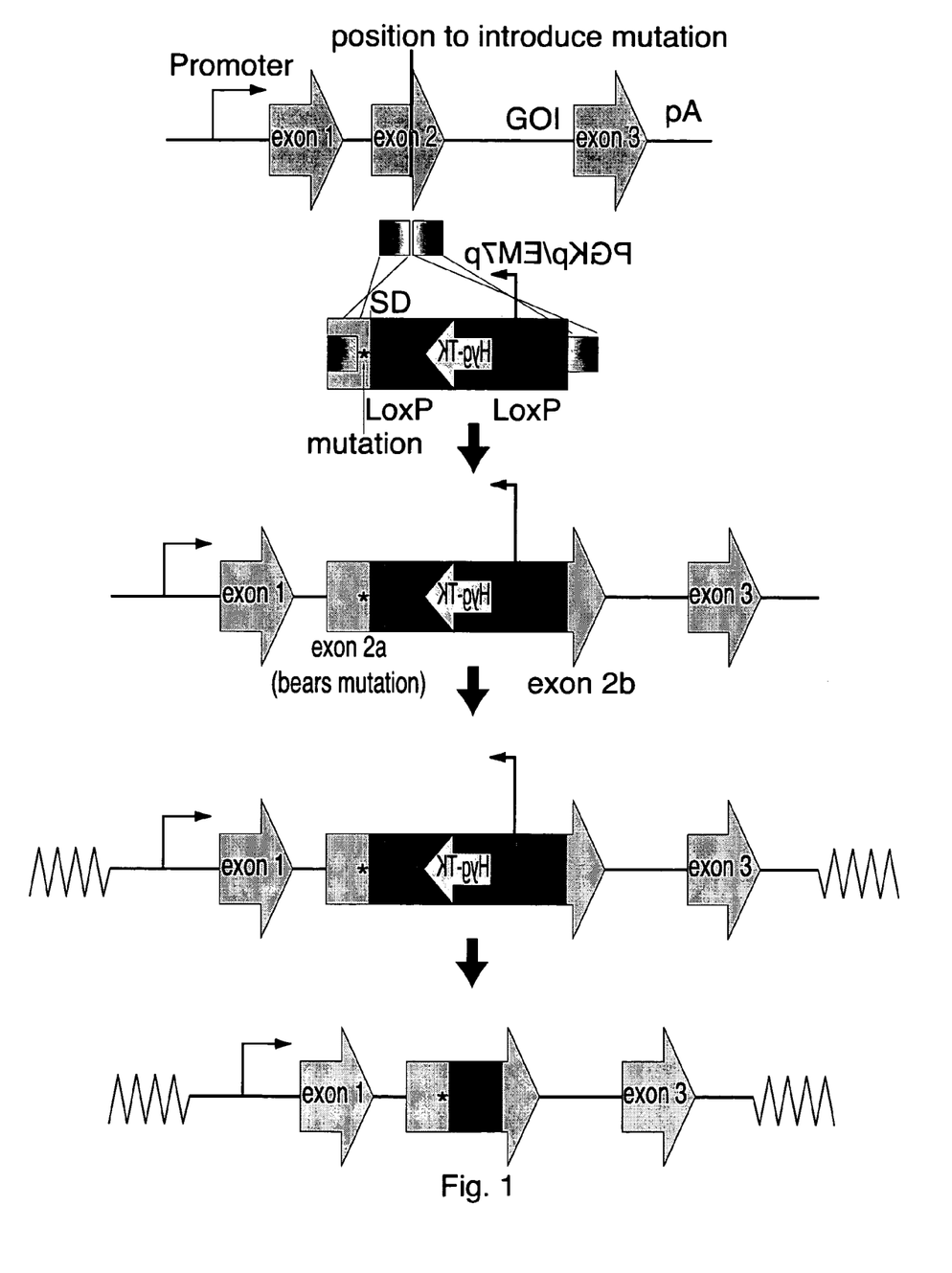

The hypothetical 3 exon gene is being modified such that a mutation is introduced within the coding sequence of exon 2 (FIG. 1). Exon 2 is, as a result of this modification, divided into two exons, exon 2a and exon 2b. In this non-limiting example, the mutation being introduced lies within exon 2a. The modification need not be in exon 2; exon 2 has been chosen only for the purpose of illustration. In addition, the modification does not need to be introduced within the coding sequence. For example, exon 2 may contain non-coding sequence that is or is part of a 5' UTR, or exon 2 may be part of a gene that does not encode a protein.

The modification is being introduced into exon 2 by the introduction of an intron. The intron is inserted into the desired position of exon 2, such that while a portion of the sequence 5' (upstream) of the intron insertion point is mutated, sufficient homology remains to allow for bacterial homologous recombination to take occur should that be the method chosen for constructing the targeting vector.

The intron employed is comprised of an antibiotic/drug selection cassette that provides antibiotic selection in prokaryotic cells and drug selection in eukaryotic cells. The components of this selection cassette are a selectable marker gene, which in this non-limiting example is the fusion protein Hygromycin phosphotransferase-herpes simplex virus thymidine kinase (Hyg-TK). The hygromycin portion provides positive selection for hygromycin resistance in both prokaryotes and eukaryotes while the TK portion provides negative selection in mammalian cells using gancyclovir. In addition, an alternative TK, termed 'ΔTK', can be also be used in this fusion protein. The advantage of using ΔTK is that it allows for transmission through the male germ line, whereas wild-type TK has been shown to create problems in this setting.

In this non-limiting example, Hyg-TK is driven by the prokaryotic promoter (EM7) and the mammalian promoter phosphoglycerate kinase promoter (PGKp). Skilled artisans will recognize that other suitable promoters could be used. The Hyg-TK is followed by a polyadenylation site (polyA). In addition, in this example, the outer boundaries of the selection cassette carry loxP site in cis (oriented in the same direction with respect to one another), to allow for excision of the cassette by Cre recombinase should that be desired. Again, skilled artisans will recognize that other recombinase systems (e.g. FRT/flp) are suitable and could be used.

The selection cassette can optionally be engineered into the intron such that the coding sequence of the selectable marker will be on the strand antisense to the coding sequence of the exon being mutated and/or modified. While not strictly necessary, it is often desirable to construct the intron this way as it reduces the need to remove the cassette (e.g. by exposure to a recombinase such as Cre) before using appropriately targeted ES cells made by the methods of the invention to generate genetically modified animals, for example, mice. If the selection cassette is placed within the intron such that it is on the sense strand, it is possible that it may be transcribed along with the modified gene of interest. As a consequence, shorter than normal transcripts or otherwise altered transcripts of the gene of interest may be generated resulting in a transcript that encodes a truncated or abnormal form of the protein of interest. If the selection cassette is placed within the intron on the sense strand, deletion of the cassette using Cre recombinase is recommended.

When engineering the selection cassette within the intron, care should be taken to avoid the consensus sequences of the 5' and 3' splice junctions, which are also commonly referred to as the splice donor and splice acceptor regions, to avoid disrupting normal function of the intron, except if such a modification is purposefully desired (for example in order to affect splicing of the target gene).

After the intron has been inserted into the exon of the gene of interest to create a targeting vector, the targeting vector is introduced into ES cells by techniques known to skilled artisans (e.g. electroporation) and appropriately targeted clones are determined using standard techniques such as those described in, for example, Joyner (1999) Gene Targeting: A Practical Approach (Hames, ed.), as well as in PCT US01/45375, the contents of which is herein specifically incorporated by reference in its entirety.

The ES cells thus generated are used directly to generate chimeric mice, or they may be optionally subjected to an additional step to remove the floxed (loxP site flanked) selection cassette. This is done by exposure to Cre recombinase to excise the floxed selection cassette, leaving behind a single loxP site within the intron. Again, skilled artisans will recognize that any other suitable site-specific recombinase system may be used in place of Cre/lox.

Irrespective of the recombinase system employed, the TK part of the selection marker is utilized for negative selection of any cells wherein the selection cassette has not been removed, thus providing a convenient means to derive a cell population that lacks the selection cassette, while retaining the desired modifications, particularly the mutation deliberately introduced into exon 2a.

Example 2

Figure 2A:
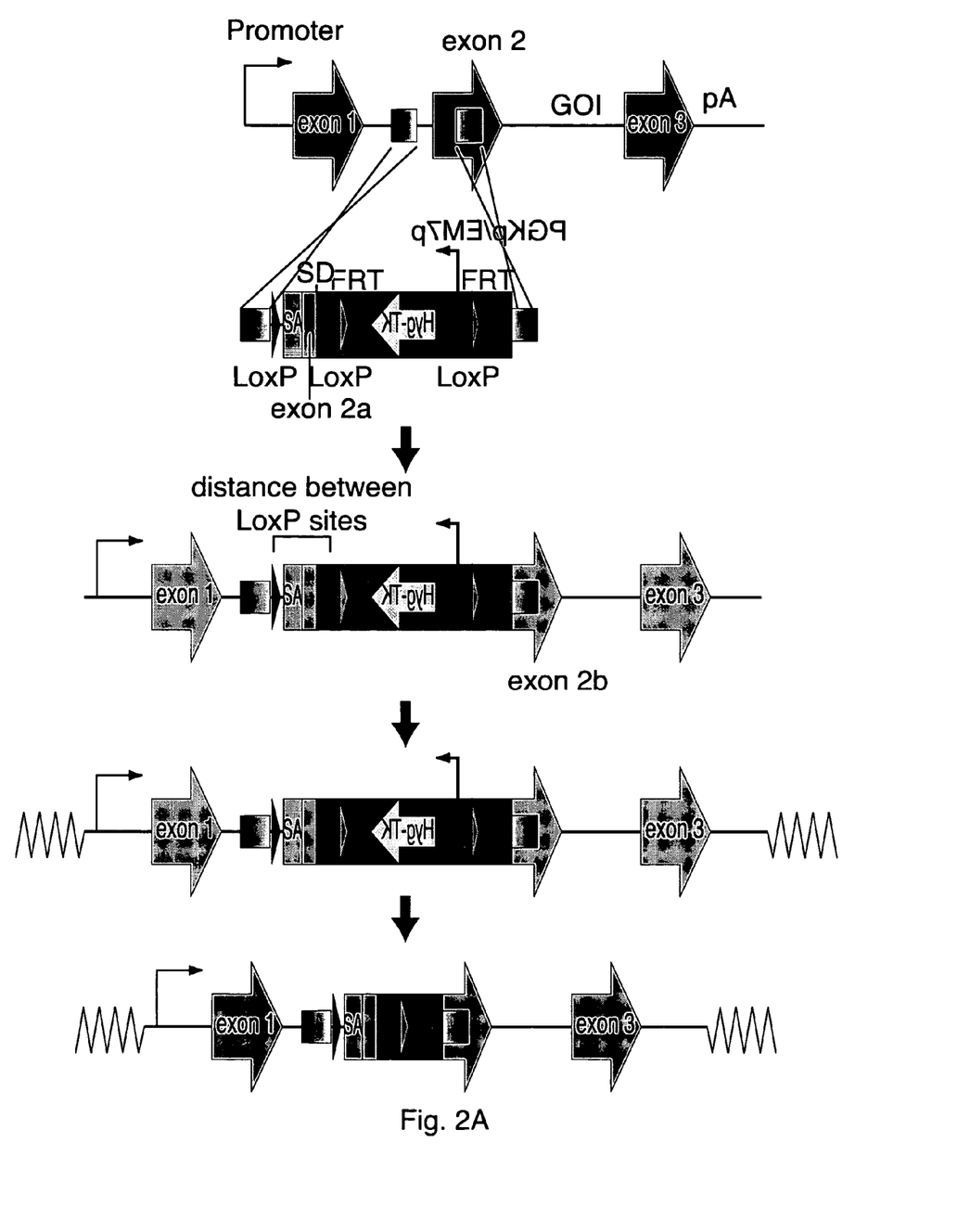
FIGS. 2A–B: Exemplary schematic diagram for introducing site-specific recombination sites into an exon by introducing an intron.

Introducing Site-specific Recombination Sites into an Exon by Introducing an Intron In this non-limiting example, a hypothetical gene comprised of 3 exons is being modified such that exon 2 is split into two exons, exon 2a and exon 2b, by introducing an intron (FIG. 2A). A loxP site is introduced upstream of the 3' splice site (or splice acceptor—SA) of intron 1 (the intron between exon 1 and exon 2a). Another loxP site is engineered inside the intron to be inserted. Thus, exon 2a is now flanked by loxP sites (called 'floxed') to create a Cre recombinase-dependent conditional allele. Because the two loxP sites are in cis (they are in the same orientation), exposure to Cre recombinase the will result in excision of the nucleotide sequence between the two loxP sites.

The features of the intron are the same as described in Example 1 above, except that the selection cassette is not only floxed, but is also flanked by FRT sites (called 'flrted"). FRT sites are recombination sites that are recognized by the Flip (Flp) recombinase. This feature allows one to remove the entire selection cassette (FIG. 2A). An alternative to this strategy is to use Cre recombinase and select for those cells were only the desired event has taken place (i.e. the selection cassette has been deleted while exon 2a has been retained.

Figure 2B:
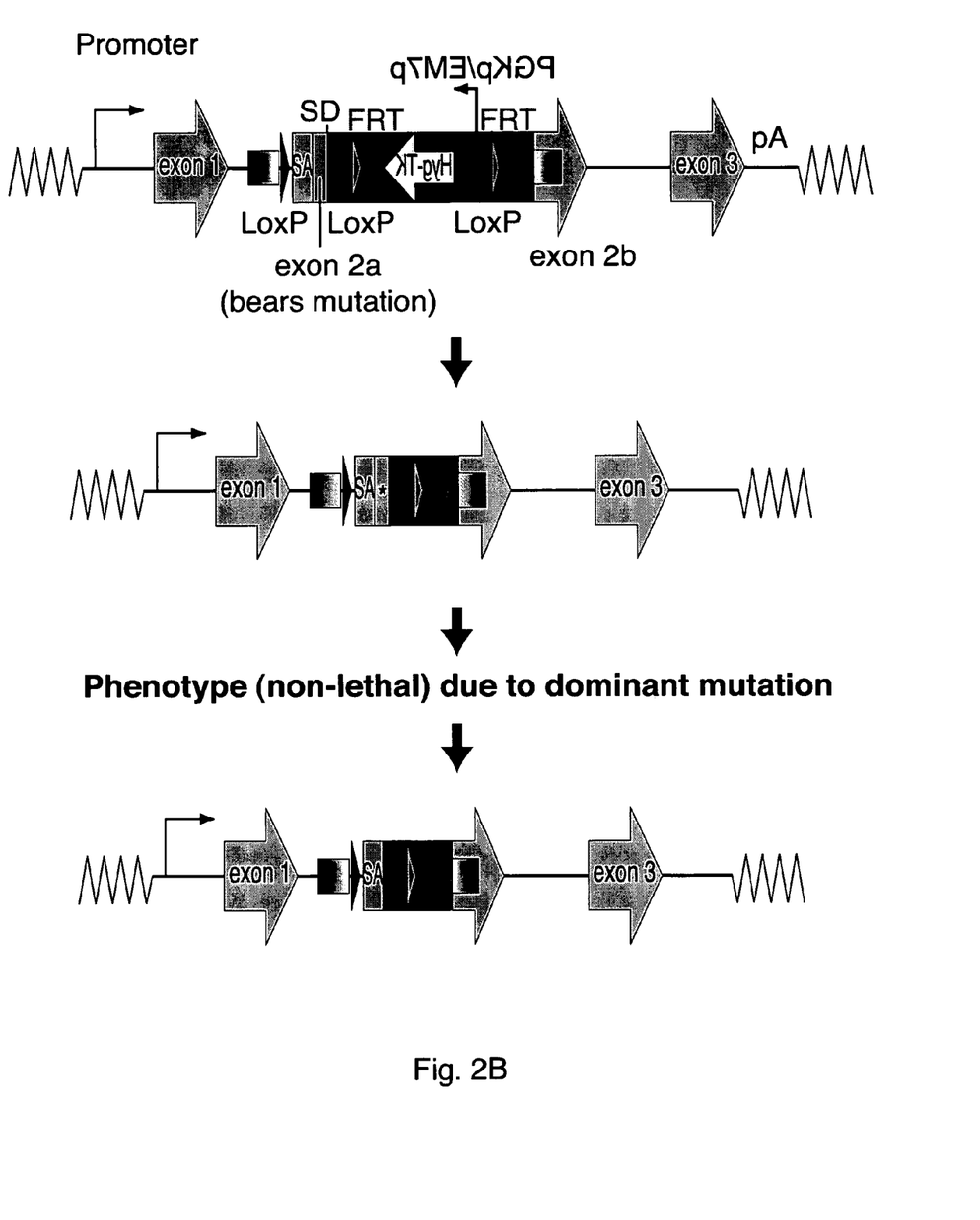

The methods described in Examples 1 and 2 can be combined to create mutant alleles that can be deleted. This strategy is particularly useful for the study of activating or dominant mutations. For example, a mutation that creates a dominant allele will result in a phenotype in heterozygous animals bearing one copy of the mutant allele and one copy of the wild-type allele. One way to demonstrate that the phenotype displayed by these animals is due to the mutation that has been introduced is to delete the mutation. This can be accomplished by flanking the mutation with site-specific recombinase sites. Prior to exposure to the recombinase the mutant form of the gene is expressed resulting in the phenotype. After exposure to the recombinase the region bearing the mutation is removed and the resulting allele no longer expresses the dominant mutant form of the gene. Barring haploinsufficiency, the phenotype displayed by the animals in whose genome the engineered mutation has been deleted should revert to wild-type (FIG. 2B).

Example 3

Figure 3A:
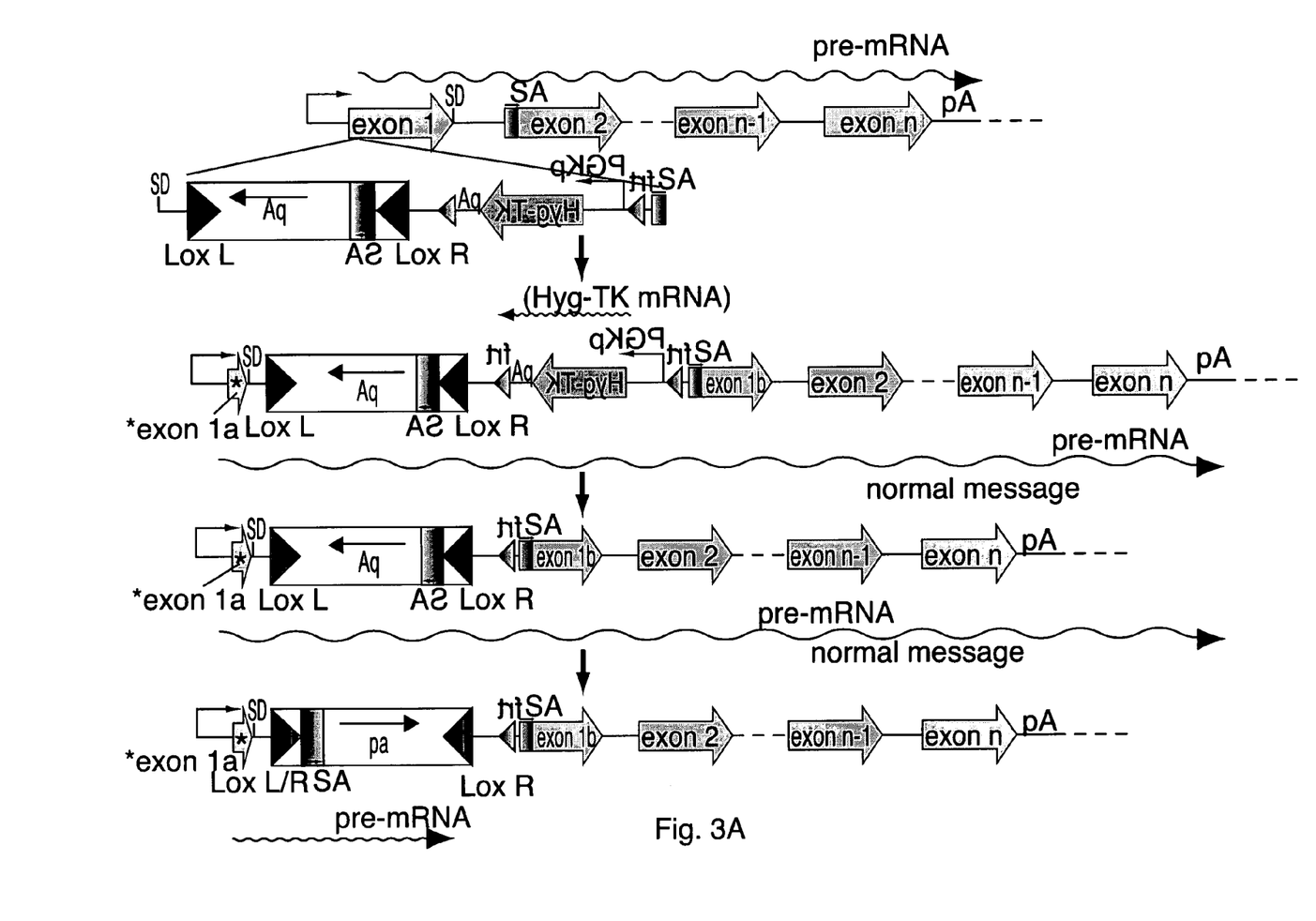

Generating a Conditional Allele by Introducing an Intron that Contains a Conditional Transcriptional Termination Signal In this non-limiting example, a hypothetical gene comprised of n-number of exons is being modified such that exon 1 is split into two exons, exon 1a and exon 1b, by introducing an intron (FIG. 3A). The intron has been genetically engineered to contain a transcriptional termination signal, in this example a polyadenylation signal sequence and site (pA), in the antisense strand. Because it is present on the antisense strand it does not alter transcription of the modified allele. Furthermore, the transcriptional termination signal is flanked by recombinase recognition sites positioned in the opposite orientation with respect to one another, as defined by their asymmetric core region such that they mediate inversion of the flanked sequence rather than deletion in the presence of their cognate recombinase. In addition, these sites are mutated such that after they have recombined the resulting sites can no longer recombine with each other, resulting in an essentially irreversible epigenetic change. In this example, the sites chosen are Lox66 and Lox71. Upon exposure to Cre recombinase, they recombine to form a mutant Lox66/71 site (which is inactive) and a wild-type LoxP site. It should be noted that this is a general property of mutant Lox sites where the mutation lies in the inverted repeats of Lox site—recombination between two mutant sites that have a mutation in the left and in the right inverted repeat, respectively, will result in a wild-type site and a double mutant Lox site in which both the left and the right inverted repeat is mutated. This property extends to mutant FRT sites, as well. To increase the efficiency of the Lox66-pA-Lox71 cassette and to reduce the likelihood of splicing around the pA site, a 3' splice site consensus sequence (SA) has been engineered immediately upstream of the pA sequence in the antisense strand. Note that this is shown here only as an example—the presence of SA is not necessary for polyadenylation and termination of transcription. Upon exposure to the cognate recombinase (in this example, Cre) the DNA sequence flanked by the Lox66 and Lox71 sites will be inverted and the transcriptional termination signal will now become part of the sense strand. As a result, the message transcribed for the modified allele will terminate at or in the vicinity of the transcriptional termination signal, resulting in a truncated version of the normal gene product. It should be noted that, depending on the placement of the transcriptional termination signal within a gene, the resulting modified allele (post-recombinase) may be a null allele, also referred to as a functional knock-out, or may be a gene product with partial activity or novel activity, such as a dominant negative or a constitutively active form or any other form of a gene that can be genetically engineered by fusing one or more new sequences to part of the existing sequence of the targeted gene.

In addition to the Lox66-pA-Lox71 cassette, the introduced intron also contains an antibiotic/drug resistance gene which in this example is a gene encoding a fusion protein consisting of hygromycin B phosphotransferase and herpes simplex thymidine kinase (Hyg-TK) driven by a mouse phosphoglycerate kinase promoter (PGKp) for expression in mammalian cells, and an EM7 promoter (EM7p) for expression in prokaryotes. The Hyg-TK open reading frame (ORF) is followed by a pA sequence. This PGKp/EM7p/Hyg-TK/pA cassette is optionally flanked by FRT sites thereby enabling removal of this cassette by FLP recombinase. It should be noted that other antibiotic/drug resistance genes familiar to the skeilled artisan can be used in place of Hyg-TK and that removal of this cassette by FLP is optional.

Figure 3B:
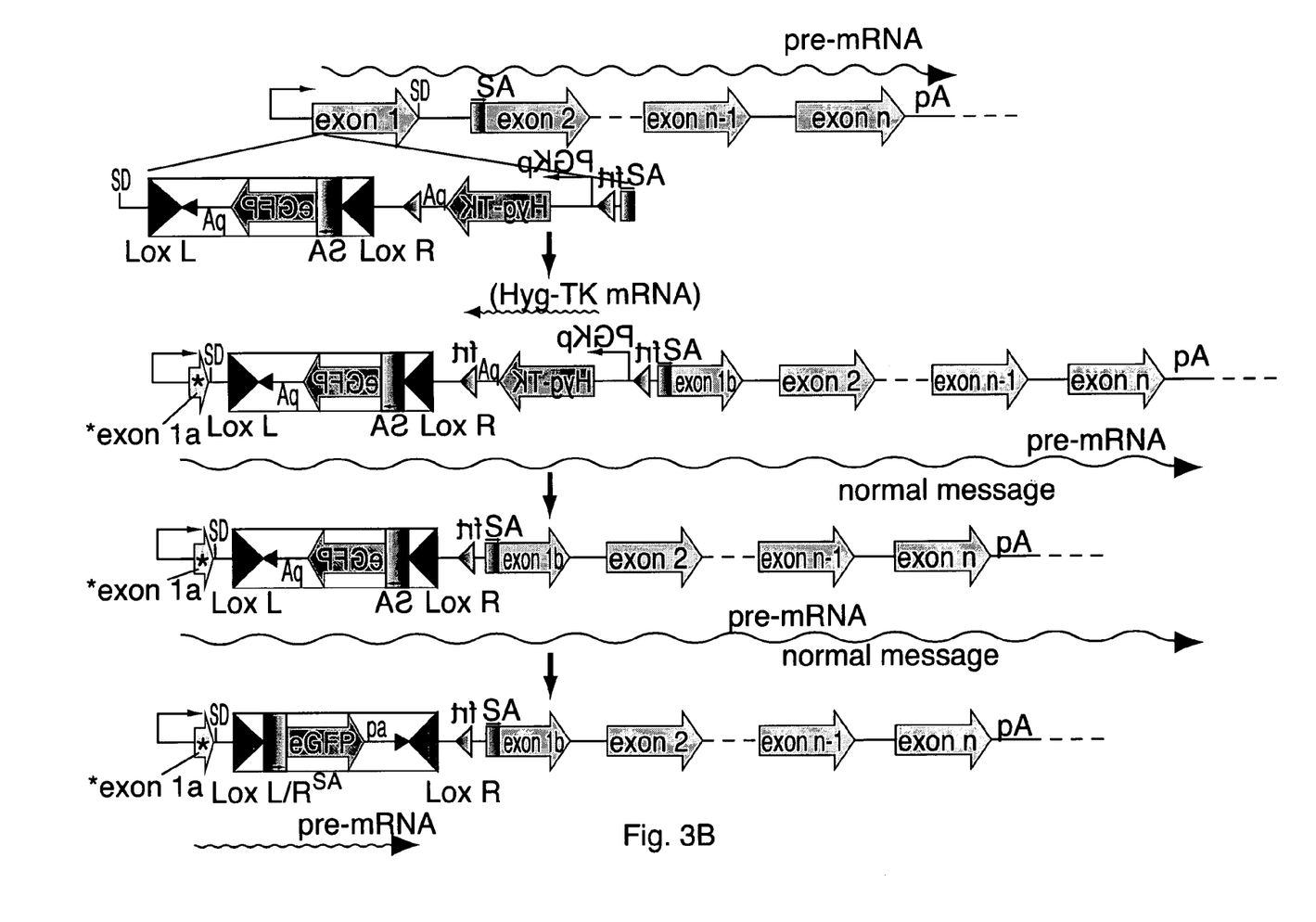

In order to facilitate visualization of the inversion event, a marker gene may be engineered into the intron. An example incorporating the marker gene eGFP is shown in FIG. 3B. The elements of the modifying intron remain the same as in the example shown in FIG. 3A except that a splice acceptor (SA)-eGFP has been incorporated between the pA and the Lox71 site in the antisense strand. The eGFP ORF is engineered in a manner such that its coding sequence will be in frame with that of the gene being modified, post Cre-mediated inversion. Pre-Cre exposure, the normal mRNA for the modified gene will be transcribed essentially identically to that of the unmodified gene, as all the elements in the engineered intron that have been incorporated into exon 2 will be spliced out of the mRNA sequence. Post-Cre exposure, a modified message will result which is composed of exons 1, 2a and the eGFP ORF, resulting in the expression of a chimeric protein that contains eGFP and which should mark the cells where the Cre-mediated inversion occurred. Alternatively, an internal ribosome entry site (IRES)-marker gene cassette could be used in place of eGFP. In this embodiment, the need to engineer the marker gene in frame with the coding sequence of the gene being modified is alleviated. In addition, not only can other marker genes can be used in place of eGFP, but this strategy can also be utilized to make novel chimeric proteins between the gene of interest and any other protein. Finally, because of the freedom of inserting the intron within any exon of a given gene (barring the rare occasion where there are gene expression control elements present within a coding exon), the desired conditional modifications can be made within any region of the gene.

Figure 3C:
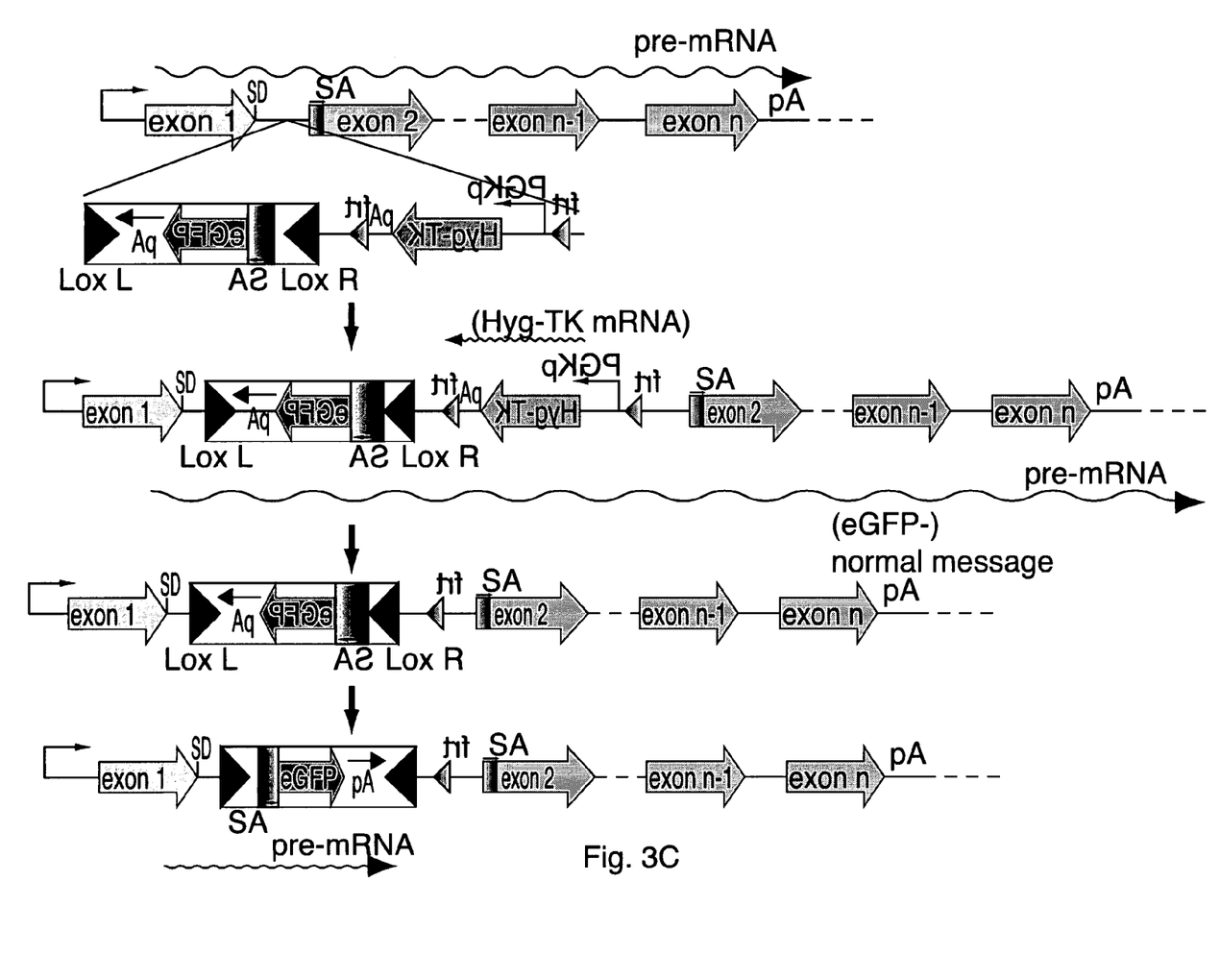

The insertion of the modified intron need not be within an exon. The elements that make up the inversion cassette (3' splice site, polyA, and the site-specific recombinase sites) can be placed within a naturally occurring intron. An example of this is shown in FIG. 3C. In this example, all of the elements are the same as those utilized in the example shown in FIG. 3B except that the insertion is within an intron therefore neither 5' nor 3' splice sites need to be introduced at the 5' and 3' ends of the inserted cassette as they will be provided by the natural intron into which the modification cassette is being inserted. As in the previous example, if a marker gene such as eGFP is utilized it is necessary to engineer the cassette such that it will be in frame with the sequence encoded by exon 1 post-inversion.

The invention claimed is:

1. An in vitro method of creating a mutation in a genomic exon in a genome of a mouse embryonic stem (ES) cell, comprising:
    a) constructing a targeting vector comprising
        (i) a 5' homology arm,
        (ii) an intron, wherein the intron comprising a drug selection cassette, wherein the drug selection cassette consists of a drug resistance gene operably linked to a promoter and flanked by a first and a second site-specific recombination sites, and
        (iii) a 3' homology arm, wherein the 5' and 3' homology arms contain sequences homologous to corresponding genomic sequences; and
    b) introducing the targeting vector into the ES cell such that the exon is mutated by the introduction of the intron.

2. The method of claim 1, wherein the first and the second site-specific recombination sites are same and oriented in the same direction with respect to one another such that excision of DNA sequence between them occurs in the presence of a suitable recombinase.

3. The method of claim 1, wherein the mutation is one or both of (i) an insertion, deletion, or substitution of one ore more nucleotides and (ii) insertion of one or more exogenous DNA sequences.

4. The method of claim 1, wherein
    the targeting vector further comprises a DNA cassette between the (i) 5' homology arm and (ii) intron, wherein the DNA cassette consists of a third site-specific recombination site, a splice acceptor sequence, and a DNA sequence homologous to a portion of the exon; and
    the intron further comprises a fourth site-specific recombination site.

5. The method of claim 4, wherein the DNA sequence comprises a mutation.

6. The method of claim 1, wherein the intron further comprises a DNA cassette upstream of the drug selection cassette, wherein the DNA cassette comprises, from 5' to 3' in order, a third site-specific recombination site, a transcription termination sequence, a splice acceptor sequence, and a fourth site-specific recombination site, wherein the transcription termination sequence and the splice acceptor sequence are in antisense orientation, and wherein the third and the fourth site-specific recombination sites are positioned in opposite orientation with respect to one another.

7. The method of claim 6, wherein the third and the fourth site-specific recombination sites are mutated such that the recombination between them cannot occur more than once.

8. The method of claim 6, wherein the DNA cassette further comprises an open reading frame between the transcription termination sequence and the splice acceptor sequence, and wherein the open reading frame is in antisense orientation.

9. The method of claim 8, wherein the open reading frame encodes a marker gene.

* * * * *